United States Patent [19]

Nickisch et al.

[11] 4,450,107

[45] May 22, 1984

[54] 7α-ALKOXYCARBONYL-15β,16β-METHYLENE-4-ANDROSTENES, PROCESS FOR THE PREPARATION THEREOF, AND USE THEREOF AS MEDICINAL AGENTS

[75] Inventors: Klaus Nickisch; Henry Laurent; Rudolf Wiechert; Jorge Casals-Stenzel, all of Berlin, Fed. Rep. of Germany

[73] Assignee: Schering Aktiengesellschaft, Berlin and Bergkamen, Fed. Rep. of Germany

[21] Appl. No.: 361,164

[22] Filed: Mar. 23, 1982

[30] Foreign Application Priority Data

Mar. 23, 1981 [DE] Fed. Rep. of Germany ....... 3111951

[51] Int. Cl.³ .............................................. A61K 31/58
[52] U.S. Cl. .................................. 424/238; 424/241; 424/243; 260/239.57; 260/397.1
[58] Field of Search ................ 549/265; 424/279, 238, 424/241; 260/239.57, 397.1

[56] References Cited

U.S. PATENT DOCUMENTS 3,787,396 1/1974 Weier et al. ............. 260/239.57
4,118,488 10/1978 Philippson et al. ........... 260/239.57
4,129,564 12/1978 Wiechert et al. ............ 260/239.57

*Primary Examiner*—Elbert L. Roberts
*Attorney, Agent, or Firm*—Millen & White

[57] ABSTRACT

7α-Alkoxycarbonyl-15β,16β-methylene-4-androstene compounds of Formula I

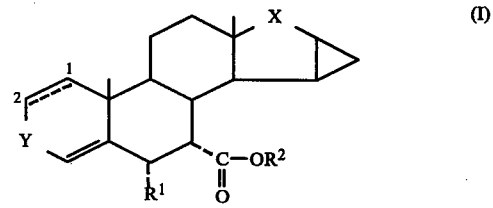

wherein
$R^1$ is hydrogen or methyl,
$R^2$ is alkyl of 1–4 carbon atoms,
X is

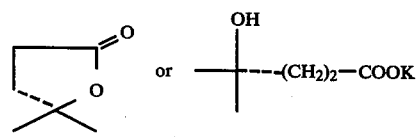

and
Y is carbonyl, and
the bond between the C-1 and C-2 carbon atoms is a single or double bond, or
when the bond between the C-1 and C-2 carbon atoms is a single bond,
X can also be

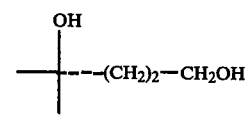

when Y is

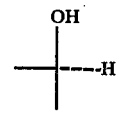

possess valuable pharmacological properties, e.g., as aldosterone antagonists, i.e. they reverse the effect of deoxycorticosterone on the excretion of sodium and potassium.

15 Claims, No Drawings

7α-ALKOXYCARBONYL-15β,16β-METHYLENE-4-ANDROSTENES, PROCESS FOR THE PREPARATION THEREOF, AND USE THEREOF AS MEDICINAL AGENTS

The present invention relates to novel 7α-alkoxycarbonyl-15β,16β-methylene-4-androstene compounds having valuable pharmacological properties.

SUMMARY OF THE INVENTION

It is an object of this invention to provide such compounds having such valuable properties.

Upon further study of the specification and appended claims, further objects and advantages of this invention will become apparent to those skilled in the art.

These objects have been attained by providing novel 7α-alkoxycarbonyl-15β,16β-methylene-4-androstene compounds of Formula I (I)

wherein
 $R^1$ is hydrogen or methyl,
 $R^2$ is alkyl of 1-4 carbon atoms,
 X is or ---(CH$_2$)$_2$—COOK and
 Y is carbonyl, and
 the bond between the C-1 and C-2 carbon atoms is a single or double bond, or
 when the bond between the C-1 and C-2 carbon atoms is a single bond,
 X can also be

---(CH$_2$)$_2$—CH$_2$OH when Y is

---H

DETAILED DISCUSSION

This invention furthermore concerns a process for preparing 7α-alkoxycarbonyl-15β,16β-methylene-4-androstene compounds of Formula I (I)

wherein
 $R^1$ is hydrogen or methyl,
 $R_2$ is alkyl of 1-4 carbon atoms,
 X is or ---(CH$_2$)$_2$—COOK and
 Y is carbonyl, and
 the bond between the C-1 and C-2 carbon atoms is single or double, or
 in addition, X is

---(CH$_2$)$_2$—CH$_2$OH

Y is

---H when the bond between the C-1 and C-2 carbon atoms is single,
 comprising conventionally reacting a compound of Formula II (II)

wherein $R^1$ is as defined above, to obtain a lower alkyl ester and, optionally, introducing a Δ$^1$-double bond and/or opening the lactone ring to obtain the corresponding propionic acid potassium salt, or reducing the latter to form the corresponding 3β,17β-dihydroxy-15β,16β-methylene-17α-(3-hydroxypropyl)-4-androstene-7α-alkoxycarbonyl compounds.

The esterification of the 7α-carboxy compounds of Formula II takes place according to conventional methods by reacting the carboxylic acid with diazoalkanes, for example with diazomethane or diazoethane, in a suitable solvent, such as diethyl ether, tetrahydrofuran, or dioxane, or in a mixture of these solvents, at a temperature of 0°–25° C., preferably 0°–5° C., whereafter excess diazoalkane is decomposed by adding an organic acid, such as glacial acetic acid or tartaric acid, and freeing the solution of the solvent under vacuum. The esterification can also be conducted by reacting, in accordance with methods known to those skilled in the art, the carboxylic acids of Formula II with an alkyl ester of chloroformic acid, e.g. butyl or isobutyl chloroformate, in a suitable solvent such as tetrahydrofuran or dioxane, in the presence of a tertiary amine, e.g. triethylamine as the HCl captor, at a temperature of 0°–20° C., preferably 0°–5° C. to obtain the mixed anhydride of general Formula III

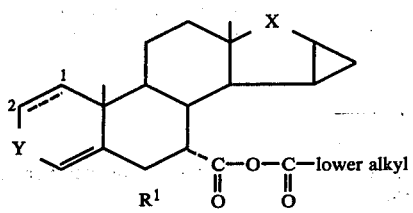

wherein $R^1$, X, and Y have the meanings indicated above.

For working-up purposes, the resultant precipitate of the tertiary amine hydrochloride is filtered off, and the filtrate is freed of the solvent, thus obtaining the mixed anhydride of Formula III as the crude product.

To obtain the desired ester of general Formula II, the compound of Formula III is dissolved in an alcohol $R^2$—OH (wherein $R^2$ has the above-mentioned meanings), heated to boiling for 24–72 hours, preferably 48 hours, and then the solvent is distilled off and the compound of Formula II is isolated.

The $\Delta^1$-double bond is introduced according to known methods by chemical or microbiological processes. Suitable chemical dehydrogenating agents for the 1,2-dehydrogenation are, for example, selenium oxide, 2,3-dichloro-5,6-dicyanobenzoquinone, chloranil, thallium triacetate, or lead tetraacetate.

Suitable microorganisms for the 1,2-dehydrogenation are, for example, Schizomycetes, especially those of the genera Arthrobacter, e.g. *A. simplex* ATCC 6946, Bacillus, e.g. *B. Lentus* ATCC 13805 and *B. sphaericus* ATCC 7055; Pseudomonas, e.g. *P. aeruginosa* IFO 3505; Flavobacterium, e.g. *F. flavenscens* IFO 3058; Lactobacillus, e.g. *L. brevis* IFO 3345; and Nocardia, e.g. *N. opaca* ATCC 4276.

The 1,2-dehydrogenation is preferably conducted by chemical methods. For this purpose, the 1,2-dihydro steroid is heated in a suitable solvent with the dehydrogenating agent over a relatively long period of time. Suitable solvents are, for example, dioxane, tert-butanol, tetrahydrofuran, toluene, benzene, or mixtures of these solvents.

The reaction is terminated after several hours. It is recommended to control the reaction by thin-layer chromatography. The reaction mixture is worked up once the starting material has been converted.

The optionally following opening of the lactone ring likewise takes place according to conventional methods. For this purpose, the lactone is heated with dilute potassium hydroxide solution, thus forming the potassium salt of the 3-substituted propionic acid.

After the reaction is terminated, the reaction mixture is worked up in the usual way, for example by precipitation, extraction, recrystallization and/or column chromatography.

If it is necessary during the course of the process of this invention to reduce the 3-carbonyl group as well as the lactone ring to the compounds according to this invention of Formula I, wherein $R^1$ and $R^2$ have the meanings given above but wherein X represents the grouping

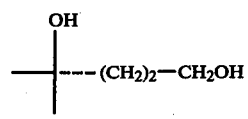

and Y represents the group

and the bond between the C-1 and C-2 carbon atoms is a single bond, then this reduction is preferably executed in stages by dissolving the 3-ketospirolactones of Formula I wherein $R^1$ and $R^2$ have the above meanings and X represents the grouping

Y is a carbonyl group, and the bond between the

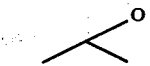

C-1 and C-2 carbon atoms is a single bond, in a suitable solvent, e.g. anhydrous diethyl ether or tetrahydrofuran, and reacting the solution at −50° to −70° C., preferably at −70° C., with a reducing agent, such as, for example, diisobutyl aluminum hydride, dissolved in toluene; and decomposing the solution with an organic acid, e.g. saturated citric acid solution, after reduction is complete, the end of which is controlled by thin-layer chromatography. After isolation of the reduction product by extraction with a water-immiscible solvent, such as methylene chloride or chloroform, washing this solution neutral with water, drying, and evaporation, the compound of general Formula IV is obtained as the crude product

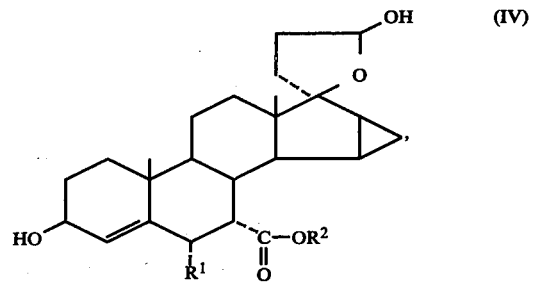

wherein $R^1$ and $R^2$ have the meanings given above.

The product is dissolved in a suitable solvent, such as, for example, isopropanol, the solution is heated several hours to boiling with a reducing agent, such as, for example, sodium borohydride or lithium aluminum tri-tert-butoxyhydride in absolute tetrahydrofuran, combined, after the reaction is completed, with dilute mineral acid, e.g. dilute sulfuric acid or phosphoric acid, and the reduction product is extracted with a water-immiscible solvent.

PREPARATION OF THE STARTING COMPOUNDS

(A)

3-(7α-Carboxy-17β-hydroxy-15β,16β-methylene-3-oxo-4-androsten-17α-yl)propionic Acid Lactone (1) 5.3 g of 3-(17β-hydroxy-15β,16β-methylene-3-oxo-4,6-androstadien-17α-yl)propionic acid lactone (prepared as in DOS No. 2,652,761) is dissolved in 100 ml of absolute tetrahydrofuran and combined under argon with 30 ml of a 2-molar solution of diethyl aluminum cyanide in toluene, refluxed for 30 minutes, cooled, and introduced into 100 ml of 1 N sodium hydroxide solution. After extraction with dichloromethane, the mixture is washed with 20% sulfuric acid and water, dried over sodium sulfate, and concentrated under vacuum. Chromatography of the crude product on silica gel with hexane/acetone yields 5 g of 3-(7α-cyano-17β-hydroxy-15β,16β-methylene-3-oxo-4-androsten-17α-yl)propionic acid lactone, mp 238°–241° C.

$\alpha_D = +68°$.

UV: $\epsilon_{235} = 14,400$.

IR: 2250, 1770, 1680, 1640, cm$^{-1}$.

(2) 5.0 g of 3-(7α-cyano-17β-hydroxy-15β,16β-methylene-3-oxo-4-androsten-17α-yl)propionic acid lactone is dissolved in 300 ml of absolute tetrahydrofuran and cooled to −70° C. The reaction mixture is combined dropwise with 35 ml of 1.2-molar diisobutyl aluminum hydride solution in toluene and agitated for 3 hours at −70° C., whereafter the mixture is decomposed with 200 ml of saturated citric acid solution, extracted with dichloromethane, washed neutral with water, dried over sodium sulfate, and concentrated under vacuum. The resultant crude product is purified by chromatography on silica gel with dichloromethane/acetone, thus obtaining 3.9 g of 3β,5′-dihydroxy-15β,16β-methylene-4-androstene-[(17β-1′)-spiro-2′]perhydrofuran-7α-carbonitrile, mp 226°–228° C.

IR: 3650, 3500, 2250, 1710 cm$^{-1}$.

(3) 3.65 g of 3β,5′-dihydroxy-15β,16β-methylene-4-androstene-[17(β-1′)-spiro-2′]perhydrofuran-7α-carbonitrile is dissolved in 75 ml of dimethyl formamide and stirred for 3 hours at room temperature with 2.25 g of imidazole and 4.05 g of tert-butyldimethylsilyl chloride, then poured into 1 liter of ice water, the resultant precipitate is filtered off, taken up in dichloromethane, dried over sodium sulfate, and concentrated under vacuum. The thus-obtained crude product is purified on silica gel with hexane/ethyl acetate, thus obtaining 4.4 g of 3,5′-bis(tert-butyldimethylsilyloxy)-15β,16β-methylene-4-androstene-[(17β-1′)-spiro-2′]perhydrofuran-7α-carbonitrile.

IR: 2250 cm$^{-1}$.

(4) 4.3 g of 3,5′-bis(tert-butyldimethylsilyloxy)-15β,16β-methylene-4-androstene-[(17β-1′)-spiro-2′]perhydrofuran-7α-carbonitrile is dissolved in 100 ml of absolute toluene and combined at −70° C. with 13 ml of 1.2-molar diisobutyl aluminum hydride solution in toluene and stirred for 3 hours at this temperature. The mixture is then decomposed with 50 ml of saturated citric acid solution, the aqueous phase is extracted with ether, the combined organic phases are washed neutral with water, dried over sodium sulfate, and concentrated under vacuum, thus obtaining 3.5 g of 3,5′-bis-(tert-butyldimethylsilyloxy)-15β,16β-methylene-4-androstene-[(17β-1′)-spiro-2′]perhydrofuran-7α-carbaldehyde.

IR: 1725 cm$^{-1}$.

(5) 1.1 g of 3,5′-bis(tert-butyldimethylsilyloxy)-15β,16β-methylene-4-androstene-[(17β-1′)-spiro-2′]perhydrofuran-7α-carbaldehyde is dissolved in 50 ml of acetone and combined at 0° C. with 2.7 ml of Jones solution and stirred at this temperature for one hour. Subsequently, the mixture is diluted with 300 ml of water and extracted with dichloromethane. The combined organic phases are extracted with 1N sodium hydroxide solution, the aqueous phase is washed with dichloromethane, acidified with cold concentrated sulfuric acid, extracted with dichloromethane, and washed neutral with water, then dried over sodium sulfate, and concentrated under vauum. Yield: 528 g of 3β-(7α-carboxy-17β-hydroxy-15β,16β-methylene-3-oxo-4-androsten-17α-yl)propionic acid lactone, mp 260°–262° C.

UV: $\epsilon_{238} = 16,900$.

(B)

3β-(7α-Carboxy-17β-hydroxy-6α-methyl-15β,16β-methylene-3-oxo-4-androsten-17α-yl)propionic Acid Lactone (1) 10 g of 3-(17β-hydroxy-15β,16β-methylene-3-oxo-4-androsten-17α-yl)propionic acid lactone (prepared as described in DOS No. 2,652,761) is added in bulk to a suspension of 19 ml of phosphorus oxychloride, 300 ml of chloroform, 10 g of sodium acetate, and 300 ml of methylal and heated to boiling. Within 2 hours, 19 ml of phosphorus oxychloride is added dropwise to the reaction mixture and the latter is boiled for another 2 hours. After cooling, saturated sodium carbonate solution is added thereto; the organic phase is separated and concentrated under vacuum. The resultant crude product is purified by chromatography on silica gel with dichloromethane/acetone, thus obtaining 7.2 g of 3-(17β-hydroxy-6,6;15β,16β-bis-methylene-3-oxo-4-androsten-17α-yl)-propionic acid lactone, mp 170.5°–172.5° C.

UV: $\epsilon_{261} = 11,300$.

(2) 7 g of 3-(17β-hydroxy-6,6;15β,16β-bis-methylene-3-oxo-4-androsten-17α-yl)propionic acid lactone is combined, in 250 ml of ethanol, with 3.5 g of anhydrous sodium acetate and 500 mg of palladium on carbon, 5%. The reaction mixture is combined under boiling with 1.4 ml of cyclohexane in 40 ml ethanol in incremental portions over a period of 8 hours. The mixture is then filtered off from the catalyst, and the filtrate is concentrated under vacuum. The resultant crude product is purified by chromatography on silica gel with dichloromethane/acetone, thus producing 5.9 g of 3-(17β-hydroxy-6-methyl-15β,16β-methylene-3-oxo-4,6-androstadien-17α-yl)propionic acid lactone, mp 228.5°–231° C.

UV: $\epsilon_{290} = 23,800$.

(3) 6.8 g of 3-(17β-hydroxy-6-methyl-15β,16β-methylene-3-oxo-4,6-androstadien-17α-yl)propionic acid lactone is combined in 150 ml of absolute tetrahydrofuran with 35 ml of a 2-molar solution of diethyl aluminum cyanide in toluene, refluxed for one hour, cooled, and introduced into 100 ml of 1 N sodium hydroxide solution. After extraction with dichloromethane, the mixture is washed with 20% sulfuric acid and water, dried over sodium sulfate, and evaporated under vacuum, thus obtaining 6.7 g of 3-(7α-cyano-17β-hydroxy-6α-methyl-15β,16β-methylene-3-oxo-4-androsten-17α-yl)propionic acid lactone as the crude product.

UV: $\epsilon_{236} = 12{,}200$.

(4) 6.3 g of 3-(7α-cyano-17β-hydroxy-6α-methyl-15β,16β-methylene-3-oxo-4-androsten-17α-yl)propionic acid lactone (crude product) is dissolved in 400 ml of absolute tetrahydrofuran and cooled to −70° C. This mixture is combined dropwise with 42 ml of 1.2-molar diisobutyl aluminum hydride solution in toluene and stirred for 3 hours at −70° C., decomposed with 200 ml of citric acid solution, extracted with dichloromethane, washed neutral with water, dried over sodium sulfate, and concentrated under vacuum. The thus-obtained crude product is purified by chromatography on silica gel with dichloromethane/acetone, yielding 5.1 g of 3β,5′-dihydroxy-6α-methyl-15β,16β-methylene-4-androstene-[(17β-1′)-spiro-2′]perhydrofuran-7α-carbonitrile.

IR: 3650, 3520, 2260, 1710 cm$^{-1}$.

(5) 5 g of 3β,5′-dihydroxy-6α-methyl-15β,16β-methylene-4-androstene-[(17β-1′)-spiro-2′]perhydrofuran-7α-carbonitrile is dissolved in 100 ml of absolute dimethylformamide and stirred with 3 g of imidazole and 5.5 g of tert-butyldimethylsilyl chloride for 3 hours at room temperature, introduced into 1,000 ml of ice water, the resultant precipitate is filtered off, taken up in dichloromethane, dried over sodium sulfate, and concentrated under vacuum, thus obtaining 6.2 g of 3,5′-bis(tert-butyldimethylsilyloxy)-6α-methyl-15β,16β-methylene-4-androstene-[(17β-1′)-spiro-2′]-perhydrofuran-7α-carbonitrile as an oil.

IR: 2260 cm$^{-1}$.

(6) 6.0 g of 3,5′-bis(tert-butyldimethylsilyloxy)-6α-methyl-15β,16β-methylene-4-androstene-[(17β-1′)-spiro-2′]perhydrofuran-7α-carbonitrile is dissolved in 150 ml of absolute toluene and combined at −70° C. with 25 ml of a 1.2-molar diisobutyl aluminum hydride solution, whereafter the mixture is stirred for one hour at −70° C. and for 2 hours at −20° C. The mixture is then decomposed with 100 ml of saturated citric acid solution, the aqueous phase is extracted with ether, the combined organic phases are washed neutral with water, dried over sodium sulfate, and concentrated under vacuum. After chromatography on silica gel with hexane/ethyl acetate, 4.9 g of 3,5′-bis(tert-butyldimethylsilyloxy)-6α-methyl-15β,16β-methylene-4-androstene-[(17β-1′)-spiro-2′]-perhydrofuran-7α-carbaldehyde is obtained as an oil.

IR: 1730 cm$^{-1}$.

(7) 4.5 g of 3,5′-bis(tert-butyldimethylsilyloxy)-6α-methyl-15β,16β-methylene-4-androstene-[(17β-1′)-spiro-2′]-perhydrofuran-7α-carbaldehyde is dissolved in 125 ml of acetone and combined at 0° C. with 10 ml of Jones solution, then stirred for 2 hours at this temperature. Subsequently, the mixture is diluted with 500 ml of water and extracted with dichloromethane. The combined organic phases are extracted with 1 N sodium hydroxide solution, the aqueous phase is washed with dichloromethane and acidified with cold concentrated sulfuric acid, extracted with dichloromethane, washed neutral with water, dried over sodium sulfate, and concentrated under vacuum, thus obtaining 2.45 g of 3β-(7α-carboxy-17β-hydroxy-6α-methyl-15β,16β-methylene-3-oxo-4-androsten-17α-yl)propionic acid lactone.

UV: $\xi_{239} = 14{,}400$

The compounds of this invention possess valuable pharmacological properties. They are, inter alia, diuretics of the type of the aldosterone antagonists, i.e. they reverse the effect of deoxycorticosterone on sodium and potassium excretion. The compounds of this invention surprisingly prove to be superior in their activities over the conventional spironolactone in the testing model of Hollmanm (G. Hollmann et al., "Tubulaere Wirkungen und renale Elimination von Spirolactonen" [Tubular Effects and Renal Elimination of Spirolactones], Naunyn-Schmiedebergs Arch. Exp. Path. Pharmak. 247: 419 [1964]; P. Marx, "Renale Wirkungen des d-Aldosterons und seines Antagonisten Spironolactons" [Renal Effects of d-Aldosterone and Its Antagonist Spironolactone], Diss. Med. Fak. FU Berlin, 1966).

The compounds of this invention are utilized according to conventional methods of galenic pharmacy for the preparation of medicinal agents for oral and parenteral administration.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g. by microencapsulation, multiple coatings, etc.

Generally, the compounds of this invention are dispensed in unit dosage form comprising 2–100 mg in a pharmaceutically acceptable carrier per unit dosage.

The dosage of the compounds of this invention for administration, e.g. to human subjects is 10–200 mg/day. In general, administration is analogous to that of spironalactone.

Suitable dosages and regimen for a given host can be determined using conventional considerations, e.g., by customary comparison of the differential activities of the subject compound and of a known agent, e.g. by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

308 mg of 3β-(7α-carboxy-17β-hydroxy-15β,16β-methylene-3-oxo-4-androsten-17α-yl)propionic acid lactone is dissolved in 10 ml of tetrahydrofuran and combined with ethereal diazomethane solution until the solution assumes a permanent yellow coloring. The excess reagent is decomposed with glacial acetic acid and concentrated under vacuum. The resultant crude product is chromatographed on silica gel with dichloromethane/acetone, yielding 275 mg of 3-(7α-methoxycarbonyl-17β-hydroxy-15β, 16β-methylene-3-oxo-4-ndrosten-17α-yl)propionic acid lactone, mp 257.5°–259° C.

UV: $\epsilon_{243} = 16,400$.

EXAMPLE 2

250 mg of 3-(7α-methoxycarbonyl-17β-hydroxy-15β,16β-methylene-3-oxo-4-androsten-17α-yl)propionic acid lactone is dissolved in 100 ml of dioxane and refluxed with 250 mg of dichlorodicyanoquinone for 4 hours, then filtered and concentrated under vacuum. The residue is taken up in chloroform, washed with water, 1 N sodium hydroxide solution, and water, dried over sodium sulfate, and concentrated under vacuum. The resultant crude product is chromatographed with dichloromethane/acetone, thus obtaining 172 mg of 3-(7α-methoxycarbonyl-17β-hydroxy-15β,16β-methylene-3-oxo-1,4-androstadien-17α-yl)propionic acid lactone.

UV: $\epsilon_{241} = 15,900$.

EXAMPLE 3

150 mg of 3β-(7α-carboxy-17β-hydroxy-15β,16β-methylene-3-oxo-4-androsten-17α-yl)propionic acid lactone is dissolved in 3 ml of absolute tetrahydrofuran, combined with 0.1 ml of triethylamine, and cooled to 0° C. The mixture is combined dropwise with 0.05 ml of butyl chloroformate and agitated for one hour at this temperature. The resultant precipitate is filtered off and concentrated under vacuum. The thus-obtained residue is dissolved in ethanol and refluxed for 48 hours. After concentration under vacuum, the product is purified by preparative layer chromatography, thus obtaining 109 mg of 3-(7α-ethoxycarbonyl-17β-hydroxy-15β,16β-methylene-3-oxo-4-androsten-17α-yl)propionic acid lactone.

IR: 1770, 1725, 1675, 1620 cm$^{-1}$.

EXAMPLE 4

150 mg of 3β-(7α-carboxy-17β-hydroxy-15β,16β-methylene-3-oxo-4-androsten-17α-yl)propionic acid lactone is dissolved in 3 ml of absolute tetrahydrofuran and combined with 0.1 ml of triethylamine, then cooled to 0° C. This mixture is combined dropwise with 0.05 ml of butyl chloroformate and agitated for one hour at this temperature, whereafter the resultant precipitate is filtered off and concentrated under vacuum. The thus-produced residue is dissolved in n-propanol and refluxed for 72 hours. After conentration under vacuum, the product is purified by preparative layer chromatography, thus obtaining 87 mg of 3-(7α-propoxycarbonyl-17β-hydroxy-15β,16β-methylene-3-oxo-4-androsten-17α-yl)propionic acid lactone.

EXAMPLE 5

205 mg of 3-(7α-methoxycarbonyl-17β-hydroxy-15β,16β-methylene-3-oxo-1,4-androstadien-17α-yl)propionic acid lactone is suspended in 2 ml of methanol and stirred with 28 mg of potassium hydroxide in 0.5 ml of water for 16 hours at room temperature and for one hour at 60° C., then concentrated under vacuum. The resultant oil is precipitated into a small amount of ethanol and with ether, thus obtaining 123 mg of the potassium salt of 3-(7α-methoxycarbonyl-17β-hydroxy-15β,16β-methylene-3-oxo-1,4-androstadien-17α-yl)-propionic acid.

EXAMPLE 6

(a) 825 mg of 3-(7α-methoxycarbonyl-17β-hydroxy-15β,16β-methylene-3-oxo-4-androsten-17α-yl)propionic acid lactone is dissolved in 20 ml of absolute tetrahydrofran and combined at −70° C. with 1.8 ml of 1.2-molar diisobutyl aluminum hydride solution in toluene, left for 2 hours at this temperature, decomposed with 25 ml of saturated citric acid, extracted with dichloromethane, washed neutral with water, dried over sodium sulfate, and concentrated under vacuum, thus obtaining 738 mg of 3β,5'-dihydroxy-15β,16β-methylene-4-androstene-[(17β-1')-spiro-2']perhydrofuran-7α-carboxylic acid methyl ester, which is further processed in the crude state.

IR: 3580, 1730 cm$^{-1}$.

(b) 730 mg of 3β,5'-dihydroxy-15β,16β-methylene-4-androstene-[(17β-1')-spiro-2']perhydrofuran-7α-carboxylic acid methyl ester is dissolved in 10 ml of isopropanol and 1 ml of water and refluxed with 150 mg of sodium borohydride for 4 hours, then combined with 20 ml of 0.1 N sulfuric acid, extracted with dichloromethane, washed neutral with water, dried over sodium sulfate, and concentrated under vacuum. The resultant crude product is purified by column chromatography on silica gel with dichloromethane/acetone, thus obtaining 662 mg of the methyl ester of 3β,17β-dihydroxy-15β,16β-methylene-17α-(3-hydroxypropyl)-4-androstene-7α-carboxylic acid.

IR: 3600, 1730 cm$^{-1}$.

EXAMPLE 7

1.2 g of 3β-(7α-carboxy-17β-hydroxy-6α-methyl-15β,16β-methylene-3-oxoandrosten-17α-yl)propionic acid lactone is dissolved in 25 ml of tetrahydrofuran and combined with ethereal diazomethane solution until the mixture assumes a permanent yellow coloring. The excess reagent is decomposed with glacial acetic acid and concentrated under vacuum. The thus-obtained crude product is chromatographed on silica gel with dichloromethane/acetone, yielding 952 mg of 3-(7α-methoxycarbonyl-17β-hydroxy-6α-methyl-15β,16β-methylene-3-oxo-4-androsten-17α-yl)propionic acid lactone.

UV: $\epsilon_{241} = 17,500$.

EXAMPLE 8

750 mg of 3-(7α-methoxycarbonyl-17β-hydroxy-6α-methyl-15β,16β-methylene-3-oxo-4-androsten-17α-yl)propionic acid lactone is dissolved in 20 ml of absolute dioxane and refluxed with 750 mg of dichlorodicyanoquinone for 4 hours, then filtered and concentrated under vacuum. The resultant crude product is chromatographed with dichloromethane/acetone, thus obtaining 552 mg of 3-(7α-methoxycarbonyl-17β-hydroxy-6α-methyl-15β,16β-methylene-3-oxo-1,4-androstadien-17α-yl)-propionic acid lactone.

UV: $\epsilon_{241} = 16,600$.

EXAMPLE 9

(a) 855 mg of 3-(7α-methoxycarbonyl-17β-hydroxy-6α-methyl-15β,16β-methylene-3-oxo-4-androsten-17α-yl)propionic acid lactone is dissolved in 20 ml of absolute tetrahydrofuran and combined at −70° C. with 1.8 ml of 1.2-molar diisobutyl aluminum hydride solution in toluene, left for 2 hours at this temperature, then decomposed with 25 ml of saturated citric acid solution, extracted with dichloromethane, washed neutral with water, dried over sodium sulfate, and concentrated under vacuum, thus obtaining 725 mg of 3β,5′-dihydroxy-6α-methyl-15β,16β-methylene-4-androstene-[(17β-1′)-spiro-2′]perhydrofuran-7α-carboxylic acid methyl ester, which is further processed in the crude state.

IR: 3550, 1730 cm$^{-1}$.

(b) 725 mg of 3β,5′-dihydroxy-6α-methyl-15β,16β-methylene-4-androstene-[17(β-1′)-spiro-2′]perhydrofuran-7α-carboxylic acid methyl ester is dissolved in 10 ml of isopropanol and 1 ml of water and refluxed with 150 mg of sodium borohydride for 4 hours, then combined with 20 ml of 0.1 N sulfuric acid, extracted with dichloromethane, washed neutral with water, dried over sodium sulfate, and concentrated under vacuum. The resultant crude product is purified by column chromatography on silica gel, yielding 642 mg of 3β,17β-dihydroxy-6α-methyl-15β,16β-methylene-17α-(3-hydroxypropyl)-4-androstene-7α-carboxylic acid methyl ester.

EXAMPLE 10

425 mg of 3-(7α-methoxycarbonyl-17β-hydroxy-15β,16β-methylene-3-oxo-4-androsten-17α-yl)propionic acid lactone is suspended in 5 ml of iso-propanol and boiled under reflux with 1 ml of potassium hydroxide (1 N in methanol) for 30 minutes. After cooling, the reaction mixture is poored into 50 ml of ether. The resultant precipitate is filtered, washed with small amounts of ether and dried under vacuum, thus obtaining 378 mg of the potassium salt of 3-(7α-methoxycarbonyl-17β-hydroxy-15β,16β-methylene-3-oxo-4-androsten-17α-yl)-propionic acid.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7α-alkoxycarbonyl-15β,16β-methylene-4-androstene of the formula

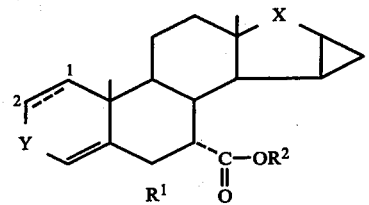

wherein
R$^1$ is hydrogen or methyl,
R$^2$ is alkyl or 1–4 carbon atoms,
(a) when the bond between the C-1 and C-2 carbon atoms is a single bond or double bond

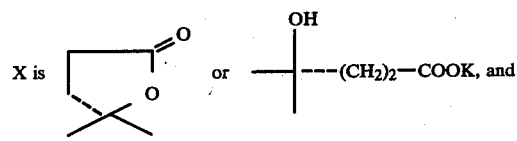

Y is carbonyl, and
(b) when the bond between the C-1 and C-2 carbon atoms is a single bond, X and Y can also be
X is

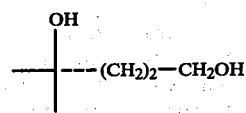

and
Y is

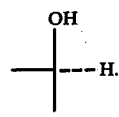

2. A compound of claim 1 wherein X is

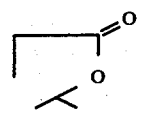

3. A compound of claim 1 wherein X is

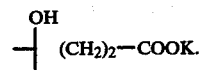

4. A compound of claim 1 wherein X is

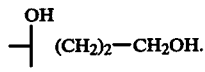

5. 3-(7α-Methoxycarbonyl)-17β-hydroxy-15β,16β-methylene-3-oxo-4-androsten-17α-yl)propionic acid lactone, a compound of claim 1.

6. 3-(7α-Methoxycarbonyl-17β-hydroxy-15β, 16β-methylene-3-oxo-1,4-androstadien-17α-yl)propionic acid lactone, a compound of claim 1.

7. Potassium salt of 3-(7α-methoxycarbonyl-17β-hydroxy-15β,16β-methylene-3-oxo-1,4-androstadien-17α-yl)-propionic acid, a compound of claim 1.

8. 3-(7α-Methoxycarbonyl-17β-hydroxy-6α-methyl-15β,16β-methylene-3-oxo-4-androsten-17α-yl)propionic acid lactone, a compound of claim 1.

9. Potassium salt of 3-(7α-methoxycarbonyl-17β-hydroxy-15β,16β-methylene-3-oxo-1,4-androstadien-17α-yl)-propionic acid, a compound of claim 1.

10. 3-(7α-Methoxycarbonyl-17β-hydroxy-6α-methyl-15β,16β-methylene-3-oxo-1,4-androstadien-17α-yl)-propionic acid lactone, a compound of claim 1.

11. A pharmaceutical composition comprising a diuretically effective amount of a compound of claim 1 and a pharmaceutically acceptable carrier.

12. A method of achieving a diuretic effect in a patient in need of such treatment comprising administering to the patient a diuretically effective amount of a compound of claim 1.

13. A compound of claim 1 wherein $C_1$-$C_2$ represents a double bond.

14. A compound of claim 1 wherein $R^1$ is methyl.

15. A compound of claim 1 wherein $C_1$-$C_2$ represents a single bond; $R^1$ is methyl; and X is

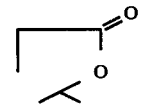

* * * * *